United States Patent [19]

Yu et al.

[11] 4,415,547

[45] Nov. 15, 1983

[54] SUSTAINED-RELEASE PHARMACEUTICAL TABLET AND PROCESS FOR PREPARATION THEREOF

[75] Inventors: Andrew B. C. Yu, Albany; Phillip M. John, East Greenbush, both of N.Y.

[73] Assignee: Sterling Drug Inc., New York, N.Y.

[21] Appl. No.: 388,435

[22] Filed: Jun. 14, 1982

[51] Int. Cl.³ .......................... A61K 9/22; A61K 9/24; A61K 9/26; A61K 9/32

[52] U.S. Cl. .......................................... 424/19; 424/20; 424/21; 424/22; 424/32; 424/33; 424/35

[58] Field of Search .................................... 424/19–22, 424/32, 33, 35

[56] References Cited

U.S. PATENT DOCUMENTS

| | | | |
|---|---|---|---|
| 2,853,420 | 9/1958 | Lowey | 424/35 |
| 2,928,770 | 3/1960 | Bardani | 424/21 |
| 2,996,431 | 8/1961 | Barry | 424/19 |
| 3,247,066 | 4/1966 | Milosovich | 424/35 |
| 3,344,029 | 9/1967 | Berger | 424/19 |
| 3,492,397 | 1/1970 | Peters et al. | 424/19 |
| 3,835,221 | 9/1974 | Fulberth et al. | 424/19 |
| 3,922,338 | 11/1975 | Estevenel | 424/19 |
| 3,950,508 | 4/1976 | Mony et al. | 424/19 |
| 4,083,949 | 4/1978 | Benedikt | 424/19 |
| 4,138,475 | 2/1979 | McAinsh et al. | 424/19 |
| 4,173,626 | 11/1979 | Dempski et al. | 424/19 |
| 4,261,970 | 4/1981 | Ogawa et al. | 424/19 |
| 4,289,795 | 9/1981 | Bogentoft et al. | 424/19 |
| 4,361,546 | 11/1982 | Stricker | 424/19 |

FOREIGN PATENT DOCUMENTS

| | | | |
|---|---|---|---|
| 109438 | 1/1940 | Australia | 424/19 |
| 2025227 | 1/1980 | United Kingdom . | |

*Primary Examiner*—Shep K. Rose
*Attorney, Agent, or Firm*—Theodore C. Miller; Paul E. Dupont; B. Woodrow Wyatt

[57] ABSTRACT

A sustained-release pharmaceutical tablet consisting essentially of drug pellets encapsulated with a water-soluble film-forming substance and a water-insoluble film-forming substance and blended and compressed into tablet form with a compressible tableting mixture and a process for preparation thereof are disclosed.

8 Claims, No Drawings

4,415,547

SUSTAINED-RELEASE PHARMACEUTICAL TABLET AND PROCESS FOR PREPARATION THEREOF

BACKGROUND OF THE INVENTION

1. Field of the Invention

The invention relates to a sustained-release pharmaceutical tablet consisting essentially of encapsulated drug pellets blended and compressed into tablet form with a compressible tableting mixture and a process for preparation thereof.

2. Description of the Prior Art

Barry U.S. Pat. No. 2,996,431 issued Aug. 15, 1961 discloses a friable tablet composed of a large number of small pellets embedded in a matrix or binder. The pellets are provided with a coating of a medicinal agent in turn sealed by a protective or barrier coating whose thickness or character is such that the protective coatings on different groups of pellets are disintegrated in the alimentary tract at successive time intervals to achieve a sustained action. The matrix or binder into which the pellets are embedded is designed to be readily disintegrable on application of thumb pressure with a twisting motion due to the shearing forces transmitted by the pellets.

Peters et al. U.S. Pat. No. 3,492,397 issued Jan. 27, 1970 discloses a method for imparting sustained-release characteristics to drug-coated pellets by coating the pellets with a combination of wax and ethylcellulose.

Fulberth et al. U.S. Pat. No. 3,835,221 issued Sept. 10, 1974 discloses a delayed-action drug dosage form wherein the active substance is applied onto small sugar globules. The drug-coated globules are provided with a release-delaying coating which is suitable as a dialysis membrane and which contains a film former polyvinyl acetate, preferably in admixture with ethylcellulose. The globules coated with active ingredient and dialysis membrane are then made up into capsules.

Estevenel et al. U.S. Pat. No. 3,922,338 issued Nov. 25, 1975 discloses tablets comprising the association of a plurality of superposed layers of which the medial layer contains microcapsules containing an active substance. The exterior layers which comprise microcrystalline cellulose, starch, alginate or polyoxyethylene glycol constitute means of protecting the microcapsules of the medial layer.

Mony et al. U.S. Pat. No. 3,950,508 issued Apr. 13, 1976 discloses the preparation of delayed-action pharmaceutical tablets from admixtures of active ingredient with talc, ethylcellulose, magnesium stearate and optionally polyvinylpyrrolidone. The mixture of ingredients is granulated and compressed into tablets.

Ogawa et al. U.S. Pat. No. 4,261,970 issued Apr. 14, 1981 from application Ser. No. 109,082 filed Jan. 2, 1980 discloses a sustained-release granule comprising theophylline in combination with the metal salt of a high fatty acid and ethylcellulose. The release rate of theophylline is stated to depend upon the ratios of theophylline, the metal salt of a higher fatty acid and ethylcellulose.

Boehringer Ingelheim British Pat. No. 2,025,227 published Jan. 23, 1980 discloses a pharmaceutical preparation in retard form comprising a core containing an active substance together with a carrier or excipient, said core being coated with a semipermeable coating comprising a water-insoluble film former, e.g. ethylcellulose, and a water-soluble polymer, e.g. polyvinylpyrrolidone. The core may be in the form of a tablet which is then spray-coated with the semipermeable coating.

SUMMARY OF THE INVENTION

In a composition of matter aspect the invention is a sustained-release pharmaceutical tablet consisting essentially of (A) from about 35% to about 85% by weight of a plurality of encapsulated pellets each consisting essentially of
  (a) from about 30% to about 98% by weight of a sugar-starch bead which is coated with
  (b) from about 1% to about 70% by weight of a first coat consisting of from about 75% to about 99% by weight of an orally administrable drug and from about 1% to about 25% by weight of a water-soluble drug-binding substance selected from the group consisting of polyvinylpyrrolidone, polyvinyl alcohol, methylcellulose and hydroxypropyl methylcellulose and
  (c) from about 1% to about 15% by weight of a second coat consisting essentially of from about 1% to about 10% by weight of a water-soluble film-forming substance selected from the group consisting of polyvinylpyrrolidone, polyvinyl alcohol, methylcellulose and hydroxypropyl methylcellulose, from about 1% to about 60% by weight of a water-insoluble film-forming substance consisting of ethylcellulose and from about 30% to about 98% by weight of a dusting powder selected from the group consisting of talc, silicon dioxide and titanium dioxide, which encapsulated pellets are blended and compressed into tablet form with (B) from about 15% to about 65% by weight of a compressible tableting mixture consisting essentially of from about 20% to about 40% by weight of a diluent selected from the group consisting of the monosaccharides and the disaccharides, from about 30% to about 50% by weight of a diluent-barrier consisting of microcrystalline cellulose, from about 10% to about 30% by weight of a binder consisting of ethylcellulose, and from about 5% to about 20% by weight of a hydrophobic lubricant selected from the group consisting of hydrogenated vegetable oil, stearic acid, magnesium stearate and calcium stearate.

In a process aspect the invention is the process of preparing a sustained-release pharmaceutical tablet which comprises blending and compressing into tablet form a mixture consisting essentially of (A) from about 35% to about 85% by weight of a plurality of encapsulated pellets each consisting essentially of
  (a) from about 30% to about 98% by weight of a sugar-starch bead which is coated with
  (b) from about 1% to about 70% by weight of a first coat consisting of from about 75% to about 99% by weight of an orally administrable drug and from about 1% to about 25% by weight of a water-soluble drug-binding substance selected from the group consisting of polyvinylpyrrolidone, polyvinyl alcohol, methylcellulose and hydroxypropyl methylcellulose and
  (c) from about 1% to about 15% by weight of a second coat consisting essentially of from about 1% to about 10% by weight of a water-soluble film-forming substance selected from the group consisting of polyvinylpyrrolidone, polyvinyl alcohol, methylcellulose and hydroxypropyl methylcellulose, from about 1% to about 60% by weight of a water-insoluble film-forming substance consisting of ethylcellulose and from about 30% to about 98% by weight of a dusting powder selected from the group consisting of talc, silicon dioxide and titanium dioxide;

wherein the first coat is formed by simultaneously applying the drug in powder form by dusting and the water-soluble drug-binding substance as a solution in a nonaqueous solvent by spraying and the second coat is formed by simultaneously applying the water-soluble film-forming substance and the water-insoluble film-forming substance as a solution in a nonaqueous solvent by spraying and the dusting powder by dusting; and (B) from about 15% to about 65% by weight of a compressible tableting mixture consisting essentially of from about 20% to about 40% by weight of a diluent selected from the group consisting of the monosaccharides and the disaccharides, from about 30% to about 50% by weight of a diluent-binder consisting of microcrystalline cellulose, from about 10% to about 30% by weight of a binder consisting of ethylcellulose, and from about 5% to about 20% by weight of a hydrophobic lubricant selected from the group consisting of hydrogenated vegetable oil, stearic acid, magnesium stearate and calcium stearate.

DETAILED DESCRIPTION OF THE INVENTION INCLUSIVE OF THE PREFERRED EMBODIMENTS

Orally administrable drug means a drug which is absorbed into the blood stream from the alimentary tract. Drugs soluble in the fluids of the alimentary tract are preferred. A particularly preferred drug is theophylline, a smooth muscle relaxant useful as a bronchodilator and especially useful in the treatment of asthma. A particular object of the invention is to provide a theophylline tablet which is taken twice daily and provides sustained release of theophylline to the blood at an effective concentration throughout the day.

Sugar-starch beads are also known as nonpareil seeds and are used in confectionery as well as in pharmacy. They are generally spheroidal in shape. A typical composition is about 65% cane sugar and about 35% corn starch. Beads of 20–25 mesh (0.84–0.71 mm. in diameter) are preferred. The beads serve as nuclei for application of the first coat of drug and drug-binding substance.

This is accomplished in a coating pan by spraying onto the beads a dilute solution of the drug-binding substance in a nonaqueous solvent and simultaneously adding the drug, which is preferably a solid, as a powder by dusting. Tumbling the beads, regulating the rates of spraying and dusting, maintaining the temperature at 40° C. or less, and directing a stream of air over the beads as needed permit simultaneous evaporation of the solvent, prevent agglomeration of the beads, and ensure a uniform coat. When the drug is theophylline, the preferred drug-binding substance is polyvinylpyrrolidone and the preferred nonaqueous solvent is ethanol. The thus coated beads provide the drug in convenient form for encapsulation, that is, formation of the second coat.

The second coat is likewise applied in a coating pan and controlled by tumbling the beads, regulating the rates of spraying and dusting, maintaining the temperature at 40° C. or less, and directing a stream of air over the beads as needed. The water-soluble film-forming substance and water-insoluble film-forming substance are each applied as a solution in a nonaqueous solvent by spraying. Preferably the same solvent is used for both and both are applied as one solution. The dusting powder, which may additionally contain a dye, is added simultaneously but preferably only during the first third of the coating process. When the drug is theophylline, the preferred water-soluble film-forming substance is polyvinylpyrrolidone, the water-insoluble film-forming substance is ethylcellulose, the preferred nonaqueous solvent is ethanol, and the preferred dusting powder is talc.

Upon contact of the thus-formed encapsulated pellets with the fluids of the alimentary tract the water-soluble substance in the second coat dissolves, leaving the water-insoluble substance as a semipermeable film and providing sustained-release of the drug through this film from the water-soluble drug-binding substance of the first coat. The rate of release of the drug can be varied by varying the relative amounts of water-soluble film-forming substance and water-insoluble film-forming substance in the second coat in a range from about 1:1 to about 1:60 and preferably in a range from about 1:1 to about 1:20.

In simulated stomach fluid (0.1 N HCl) or simulated intestinal fluid (the same 0.1 N HCl buffered to pH 7.5 after one hour) at body temperature (37° C.) and a constant rate of stirring (90 r.p.m.) (U.S.P. Paddle Method) encapsulated theophylline pellets prepared in accordance with the invention showed an initially rapid and a thereafter diminishing rate of dissolution during a seven-hour period. An objective of the invention is that the dissolution rate of the finished dosage form instead be linear or nearly linear. This is accomplished by incorporating the encapsulated pellets in a disintegration-resistant tablet matrix which decreases the initial rate and increases the final rate of dissolution of the encapsulated pellets, thus producing the desired linear or nearly linear dissolution rate. The dissolution rate of the resulting tablet is pH independent.

In the tableting mixture the preferred monosaccharide or disaccharide diluent is lactose and the preferred hydrophobic lubricant is hydrogenated vegetable oil. Blending the encapsulated pellets in the tableting mixture and compressing the resulting dispersion into tablet form are accomplished by conventional pharmaceutical techniques.

EXMAPLE 1

The following is the process for preparing 100 kilograms of sustained-release theophylline tablets in accordance with the invention. In this formulation the relative amounts of water-soluble film-forming substance (polyvinylpyrrolidone) and water-insoluble film-forming substance (ethylcellulose) in the second coat of the encapsulated pellets are in the ratio of 1:20.

Sugar-starch beads (nonpareil seeds, 20–25 mesh, 27.1 kg.) tumbled in a coating pan are simultaneously dusted with anhydrous theophylline (300 mesh, 42.9 kg.) and sprayed with a solution of polyvinylpyrrolidone (1.43 kg.) in ethanol (alcohol, 95%, 19.5 kg.). The first coat as thus constituted consists of 97% drug and 3% of drug-binding substance. The resulting pellets are dried (40° C., 5–10 hr.) and screened, first through a 12-mesh screen to remove aggregates and then over a 20-mesh screen to remove fines. The theoretical yield is 71.4 kg. of pellets of 60% theophylline content. A 3% excess of theophylline may be used to adjust for loss of theophylline on the coating pan. Nonpareil seeds of 14–18 mesh are added to the pellets if needed to adjust the theophylline content to 60%.

The 60% theophylline pellets (71.4 kg.) tumbled in a coating pan are simultaneously dusted with talc (USP, 1.28 kg.) containing blue dye (FD & C Blue No. 1 Lake Dye, 0.0129 kg.) and sprayed with a solution of polyvinylpyrrolidone (0.0570 kg.) and ethylcellulose (50 c.p.s., 1.14 kg.) in ethanol (alcohol, 95%, 27.3 kg.). The second coat as thus constituted consists of 2% water-soluble film-forming substance, 46% water-insoluble film forming substance and 52% dusting powder. The resulting encapsulated pellets are dried (40° C.) to a moisture content between 0.6% and 1.0% and screened successively through 12-mesh and 20-mesh screens. The encapsulated pellets as thus constituted consist of 37% sugar-starch beads, 60% first coat and 3% second coat. The theophylline content of the encapsulated pellets is adjusted to 56% by addition of 14–18 mesh nonpareil seeds (2.71 kg.). The theoretical yield of encapsulated 56% theophylline pellets is 76.6 kg. The theophylline content is based on the amount of theophylline (42.9 kg.) used in the first coat.

A mixture of anhydrous lactose (7.14 kg.), microcrystalline cellulose (9.14 kg.), ethylcellulose (50 c.p.s., 5.00 kg.) and hydrogenated vegetable oil (2.14 kg.) is milled, then blended with 76.6 kg. of encapsulated 56% theophylline pellets. The resulting 100 kg. of blend is compressed into tablets, each weighing 700 mg. and each containing 300 mg. of theophylline. The tableting mixture as thus constituted consists of 30% diluent, 39% diluent-binder, 21% binder and 9% hydrophobic lubricant. The tablets as thus constituted consist of 77% encapsulated pellets and 23% tableting mixture.

The following tables summarize the foregoing example.

| 60% Theophylline Pellets | Percent by Weight |
|---|---|
| Theophylline Anhydrous | 60.0 |
| Nonpareil Seeds, 20-25 mesh | 38.0 |
| Polyvinylpyrrolidone | 2.00 |
| | 100.0 |

| Encapsulated 56% Theophylline Pellets | Percent by Weight |
|---|---|
| 60% Theophylline Pellets | 93.2 |
| Polyvinylpyrrolidone | 0.0744 |
| Ethylcellulose, 50 c.p.s. | 1.49 |
| Talc | 1.67 |
| Blue Dye | 0.0169 |
| Nonpareil Seeds, 14-18 mesh | 3.54 |
| | 100.0 |

| 300-Mg. Theophylline Tablets | Mg. per Tablet |
|---|---|
| Encapsulated 56% Theophylline Pellets | 536. |
| Lactose Anhydrous | 50.0 |
| Microcrystalline Cellulose | 64.0 |
| Ethylcellulose, 50 c.p.s. | 35.0 |
| Hydrogenated Vegetable Oil | 15.0 |
| | 700. |

EXAMPLE 2

In the formulation of this example, which is summarized in the following tables, the relative amounts of water-soluble film-forming substance (polyvinylpyrrolidone) and water-insoluble film-forming substance (ethylcellulose) in the second coat of the encapsulated pellets are in the ratio of 1:1. The 60% theophylline pellets and the procedures for preparing the encapsulated pellets and tablets are the same as those described in Example 1.

| Encapsulated 56.8% Theophylline Pellets | Percent by Weight |
|---|---|
| 60% Theophylline Pellets | 94.7 |
| Polyvinylpyrrolidone* | 0.125 |
| Ethylcellulose, 50 c.p.s.* | 0.125 |
| Talc | 5.07 |
| Blue Dye | 0.0153 |
| | 100.0 |

*Applied as a single solution in ethanol (alcohol, 95%), each at a concentration of 1.25% (weight/volume).

The second coat as thus constituted consists of 2% water-soluble film-forming substance, 2% water-insoluble film-forming substance and 95% dusting powder. The encapsulated pellets as thus constituted consist of 36% sugar-starch beads, 59% first coat and 5% second coat.

| 300-Mg. Theophylline Tablets | Mg. per Tablet |
|---|---|
| Encapsulated 56.8% Theophylline Pellets | 528. |
| Lactose Anhydrous | 58.0 |
| Microcrystalline Cellulose | 64.0 |
| Ethylcellulose, 50 c.p.s. | 35.0 |
| Hydrogenated Vegetable Oil | 15.0 |
| | 700. |

The tableting mixture as thus constituted consists of 34% diluent, 37% diluent-binder, 20% binder and 9% hydrophobic lubricant. The tablets as thus constituted consist of 76% encapsulated pellets and 24% tableting mixture.

DISSOLUTION RATE STUDY

Tablets prepared in accordance with Examples 1 and 2 were tested for rate of dissolution by the above-described U.S.P. Paddle Method using for each tablet 900 ml. of 0.1 N HCl buffered to pH 7.5 after one hour. The rate of stirring was 120 r.p.m. instead of 90 r.p.m. Six tablets from each of three batches of each example were tested. The results were averaged for each example and are shown below.

EXAMPLE 1

| Hour(s) Elapsed | Percent Drug Dissolved | Percent Drug Dissolved per Hour |
|---|---|---|
| 1 | 14.5 | 14.5 |
| 3 | 37.4 | 12.5 |
| 5 | 58.5 | 11.7 |
| 8 | 79.6 | 10.0 |
| 10 | 88.0 | 8.8 |
| 12 | 94.2 | 7.9 |

EXAMPLE 2

| Hour(s) Elapsed | Percent Drug Dissolved | Percent Drug Dissolved per Hour |
|---|---|---|
| ½ | 16.1 | 32.2 |
| 1 | 30.5 | 30.5 |
| 2 | 53.9 | 27.0 |
| 3 | 66.9 | 22.3 |
| 4 | 77.0 | 19.3 |

-continued

| Hour(s) Elapsed | Percent Drug Dissolved | Percent Drug Dissolved per Hour |
|---|---|---|
| 5 | 85.4 | 17.1 |
| 6 | 90.2 | 15.0 |
| 8 | 96.1 | 12.0 |
| 10 | 101.7* | 10.2 |

*average of two batches

These results show that both formulations delivered the drug completely or nearly completely within twelve hours, that of Example 2 more rapidly and less linearly than that of Example 1. The time for dissoluton of half of the drug was about 4 hours for Example 1 and about 2 hours for Example 2.

HUMAN BIOAVAILABILITY STUDY

Bioavailability of the drug from the formulations of Examples 1 and 2 was tested in humans by administering single doses of each of them orally, taking blood samples at hourly intervals postmedication during a 24-hour period, and assaying the plasmas for theophylline concentrations. Each of the formulations was tested in ten persons. The theophylline concentrations were averaged for each group of ten persons at each hourly interval and are presented together with the standard deviations in the following table.

| Hour(s) Post-medication | Theophylline Concentration ($\mu$g./ml.) | | | |
|---|---|---|---|---|
| | Example 1 | | Example 2 | |
| | Mean | Standard Deviation | Mean | Standard Deviation |
| 1 | 0.7 | 0.6 | 1.3 | 1.0 |
| 2 | 1.9 | 1.5 | 4.2 | 2.3 |
| 4 | 4.5 | 1.7 | 6.7 | 0.8 |
| 6 | 5.1 | 1.3 | 6.1 | 0.8 |
| 8 | 4.8 | 0.9 | 5.0 | 0.7 |
| 10 | 4.2 | 0.7 | 4.0 | 0.8 |
| 12 | 3.7 | 0.6 | 3.3 | 0.8 |
| 24 | 1.1 | 0.7 | 0.9 | 0.8 |

The table shows that both formulations produced a plateau theophylline concentration of 3.3–6.7 $\mu$g./ml. 2–4 hours postmedication lasting until at least 12 hours postmedication.

The results further show that the formulation of Example 1 produced an average maximum theophylline concentration of 5.4 $\mu$g./ml. 6.6 hours postmedication in close approximation of the desired peaking time of a twice daily medication. The formulation of Example 2 produced an average maximum theophylline concentration of 6.9 $\mu$g./ml. 4.2 hours post-medication in close approximation of the desired peaking time of a thrice daily medication.

We claim:

1. A sustained-release pharmaceutical tablet consisting essentially of (A) from about 35% to about 85% by weight of a plurality of encapsulated pellets each consisting essentially of (a) from about 30% to about 98% by weight of a sugar-starch bead which is coated with (b) from about 1% to about 70% by weight of a first coat consisting of from about 75% to about 99% by weight of theophylline an orally administrable drug and from about 1% to about 25% by weight of a water-soluble drug-binding substance selected from the group consisting of polyvinylpyrrolidone, polyvinyl alcohol, methylcellulose and hydroxypropyl methycellulose and (c) from about 1% to about 15% by weight of a second coat consisting essentially of from about 1% to about 10% by weight of a water-soluble film-forming substance selected from the group consisting of polyvinylpyrrolidone, polyvinyl alcohol, methylcellulose and hydroxypropyl methylcellulose, from about 1% to about 60% by weight of a water-insoluble film-forming substance consisting of ethylcellulose and from about 30% to about 98% by weight of a dusting powder selected from the group consisting of talc, silicon dioxide and titanium dioxide, which encapsulated pellets are blended and compressed into tablet form with (B) from about 15% to about 65% by weight of a compressible tableting mixture consisting essentially of from about 20% to about 40% by weight of a diluent selected from the group consisting of the monosaccharides and the disaccharides, from about 30% to about 50% by weight of a diluent-binder consisting of microcrystalline cellulose, from about 10% to about 30% by weight of a binder consisting of ethyl cellulose, and from about 5% to about 20% by weight of a hydrophobic lubricant selected from the group consisting of hydrogenated vegetable oil, stearic acid, magnesium stearate and calcium sterate.

2. A sustained-release pharmaceutical tablet according to claim 1 wherein the water-soluble drug-binding substance is polyvinylpyrrolidone, the water-soluble film-forming substance is polyvinylpyrrolidone, the water-insoluble film-forming substance is ethylcellulose, the dusting powder is talc, the diluent is lactose, and the hydrophobic lubricant is hydrogenated vegetable oil.

3. A sustained-release pharmaceutical tablet according to claim 2 wherein the second coat contains about 2% by weight of polyvinylpyrrolidone and about 46% by weight of ethylcellulose, the encapsulated pellets contain about 56% by weight of theophylline, and the tablet contains about 77% by weight of encapsulated pellets.

4. A sustained-release pharmaceutical tablet according to claim 2 wherein the second coat contains about 2% by weight of polyvinylpyrrolidone and about 2% by weight of ethylcellulose, the encapsulated pellets contain about 56.8% by weight of theophylline, and the tablet contains about 76% by weight of encapsulated pellets.

5. The process of preparing a sustained-release pharmaceutical tablet which comprises blending and compressing into tablet form a mixture consisting essentially of (A) from about 35% to about 85% by weight of a plurality of encapsulated pellets each consisting essentially of (a) from about 30% to about 98% by weight of a sugar-starch bead which is coated with (b) from about 1% to about 70% by weight of a first coat consisting of from about 75% to about 99% by weight of theophylline an orally administrable drug and from about 1% to about 25% by weight of a water-soluble drug-binding substance selected from the group consisting of polyvinylpyrrolidone, polyvinyl alcohol, methylcellulose and hydroxypropyl methylcelluose and (c) from about 1% to about 15% by weight of a second coat consisting essentially of from about 1% to about 10% by weight of a water-soluble film-forming substance selected from the group consisting of polyvinylpyrrolidone, polyvinyl alcohol, methylcellulose and hydroxypropyl methylcellulose, from about 1% to about 60% by weight of a water-insoluble film-forming substance consisting of ethylcellulose and from about 30% to about 98% by weight of a dusting powder selected from the group consisting of talc, silicon dioxide and titanium dioxide;

wherein the first coat is formed by simultaneously applying the drug in powder form by dusting and the water-soluble drug-binding substance as a solution in a non-aqueous solvent by spraying and the second coat is formed by simultaneously applying the water-soluble film-forming substance and the water-insoluble film-forming substance as a solution in a nonaqueous solvent by spraying and the dusting powder by dusting; and (B) from about 15% to about 65% by weight of a compressible tableting mixture consisting essentially of from about 20% to about 40% by weight of a diluent selected from the group consisting of the monosaccharides and the disaccharides, from about 30% to about 50% by weight of a diluent-binder consisting of microcrystalline cellulose, from about 10% to about 30% by weight of a binder consisting of ethylcellulose, and from about 5% to about 20% by weight of a hydrophobic lubricant selected from the group consisting of hydrogenated vegetable oil, stearic acid, magnesium stearate and calcium stearate.

6. The process according to claim 5 wherein the water-soluble drug-binding substance is polyvinylpyrrolidone, the water-soluble film-forming substance is polyvinylpyrrolidone, the water-insoluble film-forming substance is ethylcellulose, the dusting powder is talc, the diluent is lactose, and the hydrophobic lubricant is hydrogenated vegetable oil.

7. The process according to claim 6 wherein the second coat contains about 2% by weight of polyvinylpyrrolidone and about 46% by weight of ethylcellulose, the encapsulated pellets contain about 56% by weight of theophylline, and the tablet contains about 77% by weight of encapsulated pellets.

8. The process according to claim 6 wherein the second coat contains about 2% by weight of polyvinylpyrrolidone and about 2% by weight of ethylcellulose, the encapsulated pellets contain about 56.8% by weight of theophylline, and the tablet contains about 76% by weight of encapsulated pellets.

* * * * *